(12) United States Patent
Green, III et al.

(10) Patent No.: US 11,433,104 B2
(45) Date of Patent: *Sep. 6, 2022

(54) AVIAN FOLLISTATIN PRODUCT

(71) Applicant: MYOS CORP., Cedar Knolls, NJ (US)

(72) Inventors: Richard Paul Green, III, San Antonio, TX (US); Richard Paul Green, Sr., Joplin, MO (US); Carlon M. Colker, Stamford, CT (US)

(73) Assignee: MYOS CORP., Cedar Knolls, NJ (US)

( * ) Notice: Subject to any disclaimer, the term of this patent is extended or adjusted under 35 U.S.C. 154(b) by 59 days.

This patent is subject to a terminal disclaimer.

(21) Appl. No.: 15/723,765

(22) Filed: Oct. 3, 2017

(65) Prior Publication Data
US 2018/0021388 A1    Jan. 25, 2018

Related U.S. Application Data

(63) Continuation of application No. 11/750,128, filed on May 17, 2007, now abandoned.

(60) Provisional application No. 60/895,405, filed on Mar. 16, 2007, provisional application No. 60/801,266, filed on May 18, 2006.

(51) Int. Cl.
| | |
|---|---|
| *A61K 35/57* | (2015.01) |
| *A23L 33/17* | (2016.01) |
| *A23L 15/00* | (2016.01) |
| *A61K 38/17* | (2006.01) |

(52) U.S. Cl.
CPC .............. *A61K 35/57* (2013.01); *A23L 15/00* (2016.08); *A23L 33/17* (2016.08); *A61K 38/1709* (2013.01); *A23V 2002/00* (2013.01)

(58) Field of Classification Search
CPC ..... A61K 35/57; A61K 38/1709; A23L 33/17; A23L 15/00; A23V 2002/00
USPC ........................................................ 435/325
See application file for complete search history.

(56) References Cited

U.S. PATENT DOCUMENTS

| | | | |
|---|---|---|---|
| 3,607,304 A | 9/1971 | Levin | 426/335 |
| 3,930,054 A | 12/1975 | Liot et al. | 426/614 |
| 5,641,517 A | 6/1997 | Eskeland et al. | 424/520 |
| 6,686,198 B1 | 2/2004 | Melton et al. | 435/377 |
| 6,921,644 B2 | 7/2005 | Duan et al. | 435/7.1 |
| 2002/0157126 A1* | 10/2002 | Lee | A61P 3/04 800/18 |

FOREIGN PATENT DOCUMENTS

| | | | |
|---|---|---|---|
| EP | 2883461 | * | 6/2015 |
| FR | 2811898 | | 7/2000 |
| WO | WO-1998-55143 A1 | | 12/1998 |

OTHER PUBLICATIONS

MedicineNet, Medical Definition of Side effects, Accessed Aug. 7, 2020, Available online at: www.medicinenet.com/script/main/art.asp?articlekey=5489.*
USDA, United States Standards, Grades, and Weight Classes for Shell Eggs, AMS 56, Effective Jul. 20, 2000, Available Online at: www.ams.usda.gov/sites/default/files/media/Shell_Egg_Standard%5B1%5D.pdf.*
Amthor et al., "Follistatin complexes Myostatin and antagonists Myostatin-mediated inhibition of myogenesis," Dev. Biol. 270:19-30 (2004).
Colker, C., "Absorption profile and hormonal influences of fertilized egg yolk ingestion in the human," J. Am. College Nutrition 25(5):Need Page Nos. (2006).
Lee, S.J. et al., Regulation of Myostatin activity and muscle growth, PNAS USA 98:9306-9311 (2001).
Patel et al., "The function of Myostatin and strategies of Myostatin blockade—new hope for therapies aimed at promoting groth of skeletal muscle," Neuromuscular Disorders 15:117-126 (2005).
Davis, C. and Reeves, R., "High value opportunities from the chicken egg," Rural Industries Research and Development Corporation Aug. 2002.
Wang, Y. et al., "Fatty Acid Determination in Chicken Egg Yolk: A Comparison of Different Methods," Poultry Science 79:1168-1171 (2000).
Case No. 308CV01654AWT Complaint and Jury Demand date Oct. 31, 2008.
Amthor, H. et al., "Follistatin regulates bone morphogenetic protein-7 (BMP-7) activity to stimulate embryonic muscle growth," Dev. Biol. 243(1):115-127 (2002).
Amthor, H. et al., "The expression and regulation of follistatin and a follistatin-like gene during avian somite compartmentalization and myogenesis," Dev. Biol. 178(2):343-362 (1996).
Asashima, M. et al., "The vegetalizing factor from chicken embryos: its EDF (activin A)-like activity," Mechanisms of Development 34(2-3):135-141 (1991).
Belecky-Adams, T.L. et al., "Activin family members in the developing chick retina: expression patterns, protein distribution, and in vitro effects," Dev. Biol. 210(1):107-123 (1999).
Chapman, S.C. et al., "Analysis of spatial and temporal gene expression patterns in blastula and gastrula stage chick embryos," Dev. Biol. 245(1):187-199 (2002).
Colker, C. et al., "Randomized Blind Comparison of Follistatin in Standard Store-Bought Unfertilized Chicken Eggs Verses Standard Store-Bought Fertile Eggs," J. Am. College Nutrition 25(5):Poster Presentations: Abstract 65 (Oct. 2006).
Connolly, D.J. et al., "Effects of follistatin and BMP4 proteins on early dorso-ventral patterning in chick," Intl. J. Dev. Biol. 44(1):129-140 (2000).

(Continued)

*Primary Examiner* — Jennifer M. H. Tichy
(74) *Attorney, Agent, or Firm* — Licata & Tyrrell P.C.

(57) ABSTRACT

Described herein are avian follistatin products, and methods for producing such products, in which such products are effective for a variety of conditions, including increasing muscle mass. Avian follistatin products described herein are packaged as dietary supplements or nutritional supplements are useful in muscle regeneration.

2 Claims, No Drawings

(56) References Cited

OTHER PUBLICATIONS

Connolly et al., "Cloning, sequencing, and expressional analysis of the chick homologue of follistatin," Dev. Genetics 17(1):65-77 (1995).

Case No. 308CV01654AWT Plaintiffs' Application for Temporary Restraining Order And Motion For Preliminary Injunction dated Dec. 30, 2008.

Kocamis, H. et al., "The ontogeny of myostatin, follistatin and activin-B mRNA expression during chicken embryonic development," Growth, Development & Aging 63(4):143-150 (1999).

Levin, "The roles of activin and follistatin signalling in chick gastrulation," Intl. J. Dev. Biol. 42(4):553-559 (1998).

Link, N.R., "Development of the avian iris and ciliary body: the role of activin and follistatin in coordination of the smooth-to-striated muscle transition," Dev. Biol. 199(2):226-234 (1998).

Link, B.a. et al., "Opposing effects of activin A and follistatin on developing skeletal muscle cells," Exp. Cell Research 233(2):350-362 (1997).

Patel, K. et al., "The role of long range, local and direct signalling molecules during chick feather bud development involving the BMPs, follistatin and the Eph receptor tyrosine kinase Eph-A4," Mechanisms of Development 86(1-2):51-62 (1999).

Office communication dated Apr. 25, 2008 from U.S. Appl. No. 11/750,128, filed May 17, 2007.

Office communication dated Jun. 6, 2008 from U.S. Appl. No. 11/750,128, filed May 17, 2007.

Office communication dated Sep. 4, 2008 from U.S. Appl. No. 11/750,128, filed May 17, 2007.

Office communication dated Oct. 30, 2008 from U.S. Appl. No. 11/750,128, filed May 17, 2007.

Office communication dated Nov. 19, 2008 from U.S. Appl. No. 11/750,128, filed May 17, 2007.

Office communication dated Dec. 24, 2008 from U.S. Appl. No. 11/750,128, filed May 17, 2007.

Office communication dated Mar. 3, 2009 from U.S. Appl. No. 11/750,128, filed May 17, 2007.

Office communication dated Nov. 8, 2013 from U.S. Appl. No. 11/750,128, filed May 17, 2007.

Office communication dated Oct. 1, 2014 from U.S. Appl. No. 11/750,128, filed May 17, 2007.

Office communication dated Mar. 24, 2015 from U.S. Appl. No. 11/750,128, filed May 17, 2007.

Office communication dated Jul. 2, 2015 from U.S. Appl. No. 11/750,128, filed May 17, 2007.

Office communication dated Aug. 4, 2015 from U.S. Appl. No. 11/750,128, filed May 17, 2007.

Office communication dated Apr. 15, 2016 from U.S. Appl. No. 11/750,128, filed May 17, 2007.

Office communication dated Aug. 26, 2016 from U.S. Appl. No. 11/750,128, filed May 17, 2007.

Office communication dated Nov. 14, 2016 from U.S. Appl. No. 11/750,128, filed May 17, 2007.

Office communication dated Apr. 3, 2017 from U.S. Appl. No. 11/750,128, filed May 17, 2007.

Froning et al. "International Egg Pasteurization Manual" United Egg Producers 2002 1-67.

* cited by examiner

AVIAN FOLLISTATIN PRODUCT

RELATED APPLICATIONS

This patent application is a continuation of U.S. application Ser. No. 11/750,128 filed May 17, 2007 which claims the benefit of provisional patent application No. 60/801,266 filed May 18, 2006 entitled "Fertilized egg protein powder (naturally occurring follistatin-based myostatin inhibitor produced in the form of a desiccated fertile egg protein powder for human or animal consumption) and naturally occurring follistatin extracted, isolated, and purified from fertile eggs." and the benefit of Provisional Patent Application No. 60/895,405 filed Mar. 16, 2007, entitled "Process for the Preparation of Avian Follistatin Product." The contents of each of these applications are incorporated by reference in their entirety.

FIELD OF THE INVENTION

Described herein are products containing follistatin, methods for preparing such products, methods for formulating such products and methods of using such products for the regulation of muscle growth.

BACKGROUND OF THE INVENTION

Wasting of skeletal muscle is a serious health condition that accompanies many conditions, diseases or disorders. Wasting of skeletal muscle also accompanies ageing. One of the most devastating but least-discussed aspects of age-related decline is the onset of frailty, i.e., the progressive loss of robustness in multiple tissues and organ systems. On the other side of the scale, many athletes benefit from an increase in muscle mass.

SUMMARY OF THE INVENTION

Strategies for muscle regeneration that lead to increased body mass are needed. Described herein are products, methods of making such products, and uses of such products to facilitate muscle regeneration and increase muscle mass. Processes for the preparation of avian follistatin product (non-albumen fecundated avian ovum decoction standardized to specific ng/ml follistatin) are described.

Described herein are compositions comprising follistatin and an egg product. In some embodiments, the composition is a sports nutrition product; in other embodiments, a dietary supplement product; in other embodiments, a nutraceutical product; in other embodiments, a health nutrition product; in other embodiments, an over-the-counter drug product; in other embodiments, a prescription drug product; and in other embodiments, a veterinarian (pet or livestock) drug product.

In a further embodiment, the egg product is derived from an avian egg. In further embodiments, the avian egg is a fertilized avian egg. In a further embodiment, the fertilized avian egg is from a domestic fowl selected from a turkey, chicken, duck, goose and ostrich. In a further embodiment, the egg product is a lyophilized, fertilized egg product. In a further embodiment, the egg product is substantially free from egg White. In a further embodiment, the egg product portion of the composition is from egg yolk. In a further or alternative embodiment, the egg product portion of the composition is from egg yolk membrane. In a further or alternative embodiment, the composition has been sterilized from a process comprising use of antibacterial agents, use of sterilizing solvent (including ethanol), use of electron beam irradiation, use of gamma irradiation, use of pasteurization, use of x-ray irradiation, use of filtration, use of membrane separation, or a combination thereof.

In a further embodiment, the egg product portion has been enriched with follistatin by a protein enhancement procedure selected from chromatography, protein extraction with solvents, ion exchange, ultrafiltration, microfiltration, or combinations thereof.

In a further embodiment, the levels of follistatin are approximated or determined in the composition using a method selected from Bradford protein assay, gel electrophoresis, mass spectrometry, microscopy, protein immunostaining, immunoprecipitation, a Western blot, spectrophotometry, an enzyme assay, ELISA, follistatin standardization, or combinations thereof.

In a further embodiment, the composition has been subjected to a procedure selected from lipid removal, carbohydrate removal, other protein removal (other than follistatin), sulfonimide removal, or combinations thereof. In a further embodiment, additional follistatin has been added to the composition (i.e., other than follistatin derived from the egg product). In a further embodiment, the composition is primarily follistatin and the other egg product portion is present in less than 50% by weight, less than 40% by weight, less than 30% by weight, less than 20% by weight, less than 10% by weight, less than 5% by weight and less than 1% by weight.

In a further embodiment, the composition is used for at least one of the following purposes: athletic performance enhancement, as a protease inhibitor, to prevent muscle atrophy, for anti-aging purposes, as an HIV medication, for the treatment of Cushings disease, for the treatment of cachexia, for the prevention of muscle wasting, for the build-up of muscle mass; for the treatment of Addison's disease, muscular dystrophy, multiple sclerosis, type I diabetes, type II diabetes, rheumatoid arthritis, Crohn's disease, ulcerative colitis, irritable bowel syndrome, other autoimmune disorders, burns, joint injury, immobilization, coma, dislocations, gastrointestinal disorders, cancer, HIV, AIDS, sarcopenia, spinal cord damage, nerve damage, TGF alpha and beta disorders, ALS, vision disorders, weak muscles, ankolosing spondilitis, anorexia, bulimia, corticosteroid use, growth factor disorders, dysphasia, SIV, body dysmorphia, low androgen levels, menstruation problems, infertility, hypo- or hyper-thyroidism, catacholamine surge, low FSH, low LH, low GRH, low HCG, and viral infections; in conjunction with surgery and/or joint replacement operations; for the improvement of weight and/or muscle mass in livestock; to raise follistatin levels in a mammal (including a human); to lower myostatin levels in a mammaol (including a human); and combinations thereof.

In a further aspect, the composition is in the form of a powder, a tablet, a capsule, an implant, an aerosol, a pudding, a gel, a paste, a syrup, a suspension, an enteric-coated product. In other embodiments, the composition is suitable for oral administration, nasal administration, inhalation administration, buccal administration, sub-buccal administration, intramuscular administration, intravenous administration, subcutaneous administration, transdermal administration, or viral delivery. In further embodiments, the composition, is micro-encapsulated, nano-encapsulated, in a vial, suitable for Monoject administration, suitable for Redi-ject administration, or suitable for air injection. In a further embodiment, the composition is in the form of a powder that can be mixed into a liquid to provide a drinkable suspension.

By way of example only, the powder can be mixed into and suspended in milk, water, juice or other liquid, to form a shake or mixed drink.

In one aspect are fertilized egg protein powders and to naturally occurring follistatin extracted, isolated, and purified from fertile eggs, i.e., a naturally occurring follistatin-based myostatin inhibitor produced in the form of a desiccated fertile egg protein powder for use. The powder is used as a dietary supplement, sports ergogenic, novel therapy for metabolic conditions, diseases with application to worldwide markets, wasting diseases, obesity, and/or obesity-related conditions. Product may be used in food, supplement, and/or encapsulated variations. Extracted, isolated, and purified follistatin may be used as a pharmaceutical through oral, intravenous, or sustained-release dosing.

In another aspect is a naturally occurring follistatin-based myostatin inhibitor produced in the form of a desiccated fertile egg protein powder for use, including by not limited to, as a dietary supplement, sports ergogenic, novel therapy for metabolic conditions, diseases with application to worldwide markets, wasting diseases, obesity, and/or obesity-related conditions.

In another aspect is the use of fertilized egg powder for producing products such as protein shake product containing bioactive peptides, or other products. Additionally, the follistatin producing membranes may be mechanically separated from the other egg components. The membranes may then be further processed to be used in the form of food supplements that contain bioactive peptides, or other products. Naturally occurring follistatin may be separated, isolated, and purified to be used as a therapeutic biopharmaceutical agent for the treatment of muscle wasting (cachexia) and other diseases.

In other embodiments, the amount of follistatin in the composition is at least 1 ng/mg of composition, 2 ng/mg of composition, 4 ng/mg of composition, 5 ng/mg of composition, 7 ng/mg of composition, 10 ng/mg of composition, 15 ng/mg of composition, 20 ng/mg of composition, 35 ng/mg of composition, 50 ng/mg of composition, 75 ng/mg of composition, 100 ng/mg of composition, 200 ng/mg of composition, 500 ng/mg of composition, 1000 ng/mg of composition, 2000 ng/mg of composition, 5000 ng/mg of composition, 10,000 ng/mg of composition, 20,000 ng/mg of composition, 50,000 ng/mg of composition, or 100,000 ng/mg of composition.

In one aspect is a composition comprising follistatin and avian egg yolk membrane, wherein the avian egg yolk membrane is substantially dehydrated and free of viable pathogens. In one embodiment, the avian egg yolk membrane is from a fertilized egg. In another embodiment, the composition comprises avian egg yolk. In a further embodiment, the avian egg yolk membrane is from a chicken egg, duck egg, or ostrich egg. In a further embodiment, the composition also comprises acceptable excipients.

In another aspect any of the aforementioned composition further comprise a component selected from whey protein, egg protein, casein, creatine, amino acids, BCAAs, carbohydrates, lipids, insulin, insulin mimics, insulin resistance products, pro-hormones, hormones, prosteroids, steroids, 7-keto DHEA, DHEA, NO enhancers, estrogen inhibitors, caffeine, stimulants, ephedrine alkaloids, vitamins, colustrum, recombinant antibodies, antibodies, growth factors, growth hormone releasing peptides, IGF1, mechano growth factor, mannitol, DMSO, or combinations thereof.

In another aspect are methods for increasing muscle mass, comprising administering to a subject any of the aforementioned compositions.

In another aspect is a process for making a follistatin-containing composition, the method comprising sterilizing an avian egg yolk or avian egg yolk membrane, wherein (i) the avian egg yolk or avian egg yolk membrane is from a fertilized avian egg; or (ii) the avian egg yolk or avian egg yolk membrane is supplemented with a composition containing follistatin.

In a further embodiment, the avian egg yolk or avian egg yolk membrane is from a fertilized avian egg. In a further embodiment, the avian egg yolk is dehydrated prior to the sterilization.

In another aspect is a process for the preparation of avian follistatin product. The avian follistatin product is a non-albumen fecundated avian ovum decoction standardized to specific ng/ml follistatin.

In one aspect is a method for the preparation of avian follistatin product that includes:
a) collecting fertilized avian egg(s);
b) cracking the collected fertilized avian egg(s) and separating the egg yolk from egg white;
c) emulsifying the egg yolk;
d) lyophilizing the emulsified egg yolk to obtain a protein powder; and
e) irradiating the protein powder obtained post lyophilization with e-beam or gamma radiation.

In a further embodiment, the process includes removal of a portion of the lipids and the carbohydrate materials from the protein powder.

In one embodiment, the method involves adding addition water during step c).

In one embodiment, the avian follistatin product is not pasteurized.

In one embodiment, the fertilized avian eggs are chicken eggs.

In aspect is a composition, comprising an avian follistatin product prepared by the method described herein. In one embodiment, the composition further includes excipients, binders or carriers. In one embodiment, the composition is in the form of a powder.

In one aspect, provided is a method for increasing muscle mass, comprising administering to a patient an avian follistatin product. In further embodiment, the administered dose (in reference to any of the aforementioned compositions) is between 10 and 2000 grams of the raw form (containing lipids and/or carbohydrates), between 20 and 1000 grams of the raw form, between, 50 and 900 grams of the raw form, between 100 and 800 grams of the raw form, between 300 and 800 grams of the raw form, between 500 and 800 grams of the raw form, or about 750 grams of the raw form. In further embodiment, the administered dose (in reference to any of the aforementioned compositions) is between 1 and 200 grams of the lipid and carbohydrate free form, between 2 and 90 grams of the lipid and carbohydrate free form, between, 5 and 80 grams of the lipid and carbohydrate free form, between 10 and 75 grams of the lipid and carbohydrate free form, between 20 and 70 grams of the lipid and carbohydrate free form, between 30 and 70 grams of the lipid and carbohydrate free form, or about 60 grams of the lipid and carbohydrate free form.

In another embodiment, provided is the use of the avian follistatin product described herein for the formulation of a nutritional supplement or a dietary supplement.

Articles of manufacture, comprising packaging material, an avian follistatin product, which is effective for increasing muscle mass or inhibiting the activity of myostatin, within the packaging material, and a label that indicates that the product is used for increasing muscle mass or for the inhibition of myostatin activity, are provided.

In some embodiments, formulations described herein are administered to a human.

In some embodiments, formulations described herein are orally administered.

Other objects, features and advantages of the methods, compounds, and compositions described herein will become apparent from the following detailed description. It should be understood, however, that the detailed description and the specific examples, while indicating specific embodiments, are given by way of illustration only, since various changes and modifications within the spirit and scope of the disclosure will become apparent to those skilled in the art from this detailed description. All references cited herein, including patents, patent applications, and publications, are hereby incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION

Wasting of skeletal muscle is not only the hallmark of many muscle disorders, but it also accompanies immobility and chronic diseases such as kidney failure, tumor cachexia and in a subset of patients with AIDS. Furthermore, decline in muscle mass is a feature of normal ageing and precipitates health problems secondary to a reduction in mobility.

Loss of muscle mass is a problem that accompanies many disorders and diseases, such as wasting disorders, traumatic disorders, inflammatory disorders, degenerative disorders, and the like. The treatments of the various disorders where muscle mass is lost usually do not improve and hasten muscle regeneration. Method of improving muscle regeneration are lacking and needed.

Methods that can stimulate muscle growth and prevent muscle loss are likely to benefit a significant proportion of the population. It may be possible to treat muscle-wasting disorders not by addressing the primary causative agent or insult, but simply by enhancing the muscle development programme.

In some embodiments, muscle regeneration may be sought for those individuals who do not suffer from muscle wasting or from disorders, diseases or conditions that cause muscle wasting. In some embodiments, muscle regeneration may be sought for performance enhancement. In other embodiments, muscle regeneration may be desirable for athletes for increasing performance. In other embodiments, muscle regeneration may be desirable for those who have low muscle mass.

One approach for muscle regeneration is through myostatin inhibition (Patel et al. "The function of Myostatin and strategies of Myostatin blockade—new hope for therapies aimed at promoting growth of skeletal muscle" *Neuromuscular Disorders* 15 (2005) 117-126).

Myostatin is an endogenous, negative regulator of muscle growth. Myostatin is a growth factor that limits muscle tissue growth, i.e. higher concentrations of myostatin in the body cause the individual to have less developed muscles. Myostatin, originally named growth differentiation factor 8, was identified through its homology to other members of the transforming growth factor-b (TGF-b) superfamily.

Human myostatin consists of two identical subunits, each consisting of 110 amino acid residues. Its total molecular weight is 25.0 kDa. The myostatin protein is produced in the skeletal muscle cells, circulates in the blood and acts on muscle tissue by apparently slowing down the development of muscle stem cells. It is expressed almost exclusively in developing and mature skeletal muscle. The precise mechanism remains unknown. Myogenic cells respond to Myostatin by down-regulating the expression of key transcriptional regulators of muscle development such as Pax-3, MyoD and Myf-5, which inhibit differentiation and further growth of muscle.

Genetically engineered mice lacking myostatin have a dramatic hypermuscular phenotype. Homozygous myostatin null mice are approximately 30% larger than their littermates, due entirely to diffusely increased muscle mass.

Other animal models with altered myostatin function confirm the importance of myostatin in postnatal muscle growth and reveal that the degree of muscle fiber hypertrophy and/or hyperplasia is in part secondary to the timing and mode of myostatin inhibition during development and postnatal life. These characteristics of myostatin deficient animals indicate that myostatin normally functions as a negative regulator of muscle growth.

Follistatin is a secreted glycoprotein that inhibits the activity of a number of TGF-b family members. There is significant data that follistatin is an in vivo inhibitor of myostatin (Armthor et al., "Follistatin complexes Myostatin and antagonizes Myostatin-mediated inhibition of myogenesis" *Dev Biol.* 2004, 270:19-30). Follistatin is a secreted protein that binds and antagonizes the function of numerous members of the TGF-b family. Deletion of the follistatin gene led to muscle loss (Matzuk M M, et al., "Multiple defects and perinatal death in mice deficient in follistatin." *Nature* 1995; 374:360-3), whereas over-expression resulted in excessive muscle growth, (Lee S J, et al., "Regulation of Myostatin activity and muscle growth." *Proc Natl Acad Sci USA* 2001; 98:9306-11). The ability of follistatin to antagonize myostatin was shown by simultaneously over-expressing both molecules in adult skeletal muscle, which prevented myostatin's ability to induce muscle loss, and recently it has been shown that follistatin and myostatin interact directly with high affinity (Amthor et al. Follistatin complexes Myostatin and antagonizes Myostatin-mediated inhibition of myogenesis. *Dev Biol* 2004; 270: 19-30).

Targeted over-expression of follistatin in skeletal muscle increased the weight of individual muscle of transgenic mice by 327% (Lee S J, et al., Regulation of Myostatin activity and muscle growth. *Proc Natl Acad Sci USA* 2001; 98:9306-11). Muscle enlargement resulted through a combination of hyperplasia (66% increase) and hypertrophy (27%). The increase in muscle mass was far greater than that observed following the deletion of the myostatin gene (McPherron A C, et al., Regulation of skeletal muscle mass in mice by a new TGF-beta superfamily member. *Nature* 1997; 387:83-90). One possible explanation for these differences is that follistatin is likely to antagonize molecules in addition to myostatin that also act as muscle growth inhibitors.

Follistatin has been identified in the yolks of fertilized avian eggs and not in the eggs of unfertilized eggs. Fertilized avian eggs may be obtained in abundance and techniques are known in the art for processing proteins from avian eggs. For example, fertilized eggs may be obtained from a hen, optionally stored in refrigerator or cold room for up to three weeks, the eggs are cracked, the yolks are separated and then processed by methods known in the art, such as lyophilization or spray drying, to provide a protein powder that is enriched with follistatin. The follistatin enriched protein powder may be subjected to electron beam or gamma irradiation for sterilization of the product.

Described herein are compositions that contain follistatin derived from fertilized avian eggs. Compositions described herein that contain follistatin are natural forms of follistatin and are not synthetic. Compositions described herein that contain follistatin may be formulated into a variety of formulations depending on the intended mode of administration.

Described herein are methods for the preparation of compositions that contain follistatin from avian eggs. Methods described herein for the preparation of compositions that contain follistatin are easily carried out and applicable on an industrial scale.

Use of Follistatin Products

Follistatin containing products may be administered to those individuals desiring or needing muscle regeneration or increases in muscle mass. In some situations, follistatin containing products may be consumed by athletes desiring an increase in muscle mass. In other situations, follistatin products may be given to the elderly, in whom muscle mass has been lost due to ageing. In other situations, muscle mass may have been lost due to health conditions, diseases or disorders and thus follistatin containing products may be beneficial to these individuals. In some other situations, follistatin containing products may be beneficial for those individuals that satisfy a number of the aforementioned conditions or situations.

Muscle Disorders

Follistatin compositions may be used in the treatment of muscle disorders, where increases in muscle mass are desired.

Muscular Dystrophies

It has been shown that myostatin blockade stimulates growth and decreases fibrosis of dystrophic muscle (K. Patel, et al., *Neuromuscular Disorders* 15 (2005) 117-126). Thus, follistatin may be used to stimulate muscle growth in muscular dystrophies.

Disuse Muscle Atrophy

Skeletal muscle will undergo rapid atrophy when its normal workload is reduced and interestingly, myostatin expression has been reported to be elevated in the muscle of patients who were bedridden for prolonged periods (Reardon K A, et al., *Muscle Nerve* 2001; 24:893-9). Muscle mass loss and atrophy also results from the process of ageing. Thus, follistatin may be used in situations where disuse muscle atrophy has occurred.

Steroid Myopathy

Glucocorticoids can induce muscle atrophy by inhibiting protein synthesis and promoting protein degradation. Administration of high doses of glucocorticoids that induce muscle atrophy have resulted in an up-regulation of myostatin expression in skeletal muscle [Ma K, et al., "Glucocorticoid-induced skeletal muscle atrophy is associated with upregulation of Myostatin gene expression" *Am J Physiol Endocrinol Metab* 2003; 285:E363-E71). Thus, follistatin may be used in steroid myopathy.

AIDS Wasting Syndrome

Serum myostatin and local myostatin levels in skeletal muscle of patients suffering from AIDS wasting syndrome have been characterized (Gonzalez-Cadavid N F, et al., *Proc Natl Acad Sci USA* 1998; 95: 14938-43). Patients with less than 10% weight loss during the past 6 month showed higher myostatin serum levels compared to healthy individuals, and patients with more than 10% weight loss showed higher levels compared to patients with less than 10% weight loss. Additionally, muscle from patients suffering from AIDS wasting syndrome contained higher levels of myostatin protein than muscle from healthy individuals. These results pointed to a correlation between muscle loss and myostatin levels in humans. Thus, follistatin may be used in aids wasting syndrome (cachexia).

Other conditions, disorders, diseases, and/or states where increases in muscle mass are needed or desired, follistatin products disclosed herein may be used.

Disclosed herein are nutritional and dietary supplements in the form of a fertilized egg protein powder or an extract of follistatin that has been isolated and purified from fertile eggs.

Disclosed herein are methods for the preparation of nutritional and dietary supplements that contain follistatin from fertilized avian eggs.

Method for the Preparation of Fertilized Egg Protein Powder

Fertilized avian eggs are obtained from hens. The eggs are collected and stored in a refrigerator or cold room (at or lower than 4° C. (40° F.)) until they are ready to be processed. The fertilized eggs are used within 3 weeks.

The following methods for the preparation of avian follistatin protein powder may be carried out using whole egg yolk or egg yolk membrane.

The processing of fertilized avian eggs is conducted using equipment and facilities that meet United States Department of Agriculture (USDA) standards for egg processing plants.

Large volumes of fertilized eggs may be processed by the following techniques. Fertilized eggs are placed on conveyor belts, washed, and then passed over a bright light source. This process is called candling. Usually blood, if present, can be observed and the egg is removed by attendants. Electronic sensing equipment may also be used to detect blood spots. The clean eggs are then automatically placed into an egg-cracking machine. Such a machine consists of a series of individual egg holders that crack the egg, separate the yolk and white, and dump each component into a separate pipe. Such a machine can process thousands of eggs an hour, and operators typically monitor the machine to detect eggs which do not separate properly or contain blood spots. If such a situation, arises, the attendants may discard the eggs that do not separate properly or contain blood spots.

The combined egg yolks, or egg yolk membranes, are then homogenized or agitated strongly to form an emulsion. The agitation may be carried out by means of a mechanical stirrer. If desired, water may be added to the homogenizer. The emulsified egg yolks are then transferred to a flask or other suitable container that has an adapter for connecting to a high vacuum apparatus (such as a mechanical oil pump). The yolk emulsion is frozen. A vacuum is applied at any stage, before, during or after the yolks are frozen.

The follistatin powder that is obtained after lyophilization is complete is transferred to any suitable container.

The follistatin protein powder that is obtained is not pasteurized.

The follistatin protein powder is then irradiated with Ebeam or gamma irradiation at levels of at least 27.5 kilo grades. The product, post lyophilization and irradiation, is pathogen tested to CDER and CBER standards.

Quality assurance is then conducted to determine the follistatin content of the protein powder. In some embodiments, the protein powder is analyzed using mass spectrometric methods and/or ELISA.

The follistatin protein powder is then processed by methods known in the art or as described herein and stored. The final formulation is in compliance with standards set forth by government agencies, such as the Food and Drug Administration (FDA).

The final form of the product is capsulated, bottled, gel packed and or otherwise contained/delivered to FDA standards.

Certain Terminology

Unless defined otherwise, all technical and scientific terms used herein have the same meaning as is commonly understood by one of skill in the art to which the claimed subject matter belongs. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

It is to be understood that the methods and compositions described herein are not limited to the particular methodology described herein and as such may vary. It is also to be understood that the terminology used herein is for the purpose of describing particular embodiments only, and is not intended to limit the scope of the methods, compositions described herein.

"Biologically-acceptable" refers to being safe for human consumption.

"Avian" refers to the class of animals named "birds". All birds lay amniotic eggs and thus eggs from any bird is contemplated for use in the methods and compositions described herein. In some embodiments, eggs are obtained from, but not limited to, domestic chicken, geese, pheasants, turkeys, ducks, emus, ostriches, pigeons, grouse, quails, doves, woodcocks, songbirds, finches. In some embodiments, avian refers to, chicken, duck, goose, ostrich, and/or turkey. In some embodiments, avian refers to chicken.

As used herein, amelioration of the symptoms of a particular disease, disorder or condition by administration of a particular composition (e.g. containing follistatin) refers to any lessening of severity, delay in onset, slowing of progression, or shortening of duration, whether permanent or temporary, lasting or transient that can be attributed to or associated with administration of the compound or composition.

The term "modulate," as used herein, means to interact with a target either directly or indirectly so as to alter the activity of the target, including, by way of example only, to inhibit the activity of the target, to limit the activity of the target, or to reduce the activity of the target. In some embodiments, the target is myostatin.

As used herein, the term "target activity" refers to a biological activity capable of being modulated. Certain exemplary target activities include but are not limited to, muscle regeneration.

As used herein, the term "antagonist" or "antagonize" refers to a compound, the presence of which results in a decrease in the magnitude of a biological activity of a protein. In certain embodiments, the presence of an antagonist results in complete inhibition of a biological activity of a protein, such as, for example, myostatin.

The term "acceptable" with respect to a formulation, composition or ingredient, as used herein, means having no persistent detrimental effect on the general health of the subject being treated.

By "pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

"Bioavailability" refers to the percentage of the weight of follistatin disclosed herein, that is delivered into the general circulation of the animal or human being studied. The total exposure (AUC(0-∞)) of a drug when administered intravenously is usually defined as 100% bioavailable (F %). "Oral bioavailability" refers to the extent to follistatin is absorbed into the general circulation when the formulation is taken orally as compared to intravenous injection.

"Blood plasma concentration" refers to the concentration of follistatin disclosed herein, in the plasma component of blood of a subject.

A measurable serum concentration or measurable plasma concentration describes the blood serum or blood plasma concentration, typically measured in mg, µg, or ng of therapeutic agent per ml, dl, or l of blood serum, absorbed into the bloodstream after administration. As used herein, measurable plasma concentrations are typically measured in ng/ml or µg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Absorption" refers to the process of movement of follistatin from site of administration across a barrier into a blood vessel or the site of action, e.g., follistatin moving from the gastrointestinal tract into the portal vein or lymphatic system.

The terms "effective amount" or "therapeutically effective amount," as used herein, refer to a sufficient amount of an agent, or composition being administered which will relieve to some extent one or more of the symptoms of the disease, disorder or condition being treated. For example, an "effective amount" for therapeutic uses is the amount of the avian follistatin product described herein required to provide a clinically significant increase in muscle mass. An appropriate "effective" amount in any individual case may be determined using techniques known in the art.

Examples of Compositions and Methods of Administration

The compositions described herein can be formulated for administration to a subject via any conventional means including, but not limited to, oral, or buccal. As used herein, the term "subject" is used to mean an animal, preferably a mammal, including a human or non-human. The terms patient and subject may be used interchangeably.

Moreover, the follistatin containing compositions described herein, can be formulated into any suitable dosage form, including but not limited to, aqueous oral dispersions, liquids, gels, syrups, elixirs, slurries, suspensions and the like, for oral ingestion by an individual in need, solid oral dosage forms, controlled release formulations, fast melt formulations, effervescent formulations, lyophilized formulations, tablets, powders, pills, dragees, capsules, delayed release formulations, aqueous liquid dispersions, self-emulsifying dispersions, solid solutions, liposomal dispersions, solid dosage forms, powders, tablets, capsules, pills, delayed release formulations.

Formulations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Formulations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, pellets, granules. In other embodiments, the pharmaceutical formulation is in the form of a powder. In still other embodiments, the pharmaceutical formulation is in the form of a tablet. Additionally, formulations described herein may be administered as a single capsule or in multiple capsule dosage form. In some embodiments, the formulation is administered in two, or three, or four, capsules or tablets.

Soft gel or soft gelatin capsules may be prepared, for example, without limitation, by dispersing the formulation in an appropriate vehicle (vegetable oils are commonly used) to form a high viscosity mixture. This mixture is then encapsulated with a gelatin based film using technology and machinery known to those in the soft gel industry. The industrial units so formed are then dried to constant weight.

In some embodiments, the formulations may include other medicinal or pharmaceutical agents, carriers, diluents, dispersing agents, suspending agents, thickening agents, adjuvants, such as preserving, stabilizing, wetting or emulsifying agents, solution promoters, and/or buffers. In addition, the formulations can also contain other therapeutically valuable substances.

The formulations described herein can include follistatin product and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, a film coating is provided around the formulation of the compound described herein. In one embodiment, some or all of the particles of the compound described herein are coated. In another embodiment, some or all of the particles of the compound described herein are microencapsulated. In still another embodiment, the particles of the compound described herein are not microencapsulated and are uncoated.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Formulations including avian follistatin product described herein may be manufactured in a conventional manner, such as, by way of example only, by means of conventional mixing, dissolving, granulating, dragee-making, levigating, emulsifying, encapsulating, entrapping or compression processes.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

In certain embodiments, compositions provided herein may also include one or more preservatives to inhibit microbial activity. Suitable preservatives include mercurycontaining substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

The term "carrier," as used herein, refers to relatively nontoxic chemical compounds or agents that facilitate the incorporation of a compound into cells or tissues, and include, e.g., binders, suspending agents, disintegration agents, filling agents, surfactants, solubilizers, stabilizers, lubricants, wetting agents, diluents, and the like.

"Dispersing agents," and/or "viscosity modulating agents" include materials that control the diffusion and homogeneity of a compound through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizcers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm$^3$, e.g. Avicel, powdered cellulose), and talc.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Flavoring agents and/or sweeteners useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

In some embodiments, solid dosage forms, e.g., tablets, capsules, are prepared by mixing avian follistatin products described herein, with one or more pharmaceutical excipients to form a bulk blend composition. When referring to these bulk blend compositions as homogeneous, it is meant that the particles of avian follistatin products described herein, are dispersed evenly throughout the composition so that the composition may be readily subdivided into equally effective unit dosage forms, such as tablets, pills, and capsules.

Conventional techniques include, e.g., one or a combination of methods: (1) dry mixing, (2) direct compression, (3) milling, (4) dry or non-aqueous granulation, (5) wet granulation, or (6) fusion. See, e.g., Lachman et al., "The Theory and Practice of Industrial Pharmacy" (1986).

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

It should be appreciated that there is considerable overlap between additives used in the solid dosage forms described herein. Thus, the above-listed additives should be taken as merely exemplary, and not limiting, of the types of additives that can be included.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials which sufficiently isolate the compound from other non-compatible excipients. Materials compatible avian follistatin products described herein are those that delay the release of the follistatin product in vivo.

Exemplary microencapsulation materials useful for delaying the release of the formulations described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In other embodiments, a powder including the formulations with an avian follistatin product described herein may be formulated to include one or more excipients and flavors. Such a powder may be prepared, for example, by mixing the formulation and optional excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When such salts are added to water, the acids and the base react to liberate carbon dioxide gas, thereby causing “effervescence.” Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, the formulations described herein, which include avian follistatin product described herein, are solid dispersions. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl 2004/0013734. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components. The enteric coated oral dosage form may also be a capsule (coated or uncoated) containing pellets, beads or granules of the solid carrier or the composition.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating for the methods and compositions described herein to achieve delivery to the lower gastrointestinal tract.

In some embodiments, formulations are provided that include particles of the avian follistatin product described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of the avian follistatin product described herein, the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC- SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethylcellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.001% to about 1.0% the volume of the aqueous dispersion. In another embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Buccal formulations that include avian follistatin product described herein may be administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with the follistatin product described herein, and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

Examples of Methods of Dosing and Treatment Regimens

The compositions containing the avian follistatin products described herein can be administered for prophylactic and/or therapeutic treatments. In therapeutic applications, the compositions are administered to a patient already suffering from a disease or condition, in an amount sufficient to improve muscle mass. Amounts effective for this use will depend on the severity and course of the disease or condition, previous therapy, the patient's health status, weight, and the judgment of the treating health care provider.

In prophylactic applications, compositions containing the avian follistatin products described herein are administered to a patient requiring or desiring increase in muscle mass. In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the health care provider.

In the case wherein the patient's condition does not improve, upon the health care provider's discretion the administration of the compounds may be administered chronically, that is, for an extended period of time, including throughout the duration of the patient's life in order to ameliorate or otherwise control or limit the symptoms of the patient's disease or condition.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, bags, containers, bottles, and any packaging material suitable for a selected formulation and intended mode of administration and treatment. A wide array of formulations of the compounds and compositions provided herein are contemplated as are a variety of treatments for any disease, disorder, or condition that would benefit by administration of follistatin and increases in muscle regeneration.

Such kits or article of manufacture optionally include a formulation as described herein with an identifying description or label or instructions relating to its use in the methods described herein.

A kit will typically may include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, carrier, package, container, labels listing contents and/or instructions for use, and package inserts with instructions for use. A set of instructions will also typically be included.

A label can be on or associated with the container. A label can be used to indicate that the contents are to be used for a specific therapeutic application. The label can also indicate directions for use of the contents, such as in the methods described herein.

The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing the follistatin products described herein formulated in a compatible carrier can also be prepared, placed in an appropriate container, and labeled for treatment of an indicated condition.

EXAMPLES

These examples are provided for illustrative purposes only and not to limit the scope of the claims provided herein.

Example 1

Determination of Follistatin Levels in Chicken Eggs

To determine the follistatin levels in conventional fertilized and non-fertilized conventional store bought chicken eggs were obtained and follistatin levels in the eggs were determined via immobilizing follistatin via binding to Activin in a C18 HPLC column (ExpertTox, Inc., Deer Park, Tex.). The assay was standardized with Recombinant Follistatin 288 and was assayed in an LC/MS with a third degree fragmentation (D. S., Tanetta, et al. 1977). Results revealed all fertile eggs contained significant concentrations of follistatin (0.11, 1.05. 0.67. and 0.81 mcg/mg) whereas two unfertilized eggs that were also tested contained no detectable follistatin (0 and 0 mcg/mg).

Example 2

Measurement of Follistatin Levels in Humans

The following assay was then conducted to determine whether orally ingested naturally occurring follistatin is absorbed and is pharmaco-kinetically active in a human model. A male subject was chosen because the normal baseline male physiology does not regularly contain any measurable concentration of follistatin.

Follistatin-rich fertile egg yolk powder properly processed to preserve active follistatin (Folstaxan™) was obtained (Celidyne Biopharma, San Antonio, Tex.). After initial blood draw and subsequent oral Folstaxan™ dosing, serum follistatin levels were qualitatively and quantitatively measured as an indicator of absorption. Because follistatin is a negative modulator of myostatin, serum myostatin levels were qualitatively and quantitatively measured as an indicator hormonal influence and thus true pharmacokinetic activity. Testing utilized a purchased follistatin and myostatin standard for verification. Confirmations were run by ELISA and quantitations by Liquid Chromatography Tandem Mass Spectrometer with third degree fragmentation (Expertox, Deer Park, Tex.)

Results showed a predicted zero level of follistatin at baseline with a myostatin level of 46 pg/ml. Within twelve hours after Folstaxan™ dosing, serum follistatin measured 57.1 pg/ml with a decline of myostatin to 34 pg/ml. Twenty four hours after the initial dosing, follistatin levels began to predictably drop from the time of initial dosing to 11.4 pg/ml, yet myostatin continued to decline slightly with a twenty four hour level of 31 pg/ml. These results indicate that a fertile egg yolk powder properly processed to preserve active follistatin, when orally ingested, results in detectable serum follistatin. Furthermore, this resultant follistatin presence has significant pharmacokinetic activity as shown by the hormonal down-regulation of serum myostatin.

Example 3

Effect of Pasteurization of Fertilized Egg Yolks on Follistatin

Fertile egg yolks contain significant concentrations of follistatin. Egg products are usually pasteurized in order to minimize danger of microbe ingestion. In an effort to identify whether pasteurization denatures or affects this source of naturally occurring follistatin, this study was undertaken.

Fertile chicken eggs were cracked and separated using commercial breakers and separators. The separated yolk was then pasteurized a HTST at 192 F (89 C) for 1.75 minutes. The egg yolks were tested for quantity and quality of active follistatin. Testing utilized purchased follistatin standardized for verification. Confirmations were run by ELISA and quantitations by Liquid Chromatography Tandem Mass Spectrometer with third degree fragmentation (Expertox, Deer Park, Tex.).

Results showed no measurable active or viable follistatin. This compares with previous results follistatin levels of 0.11 to 1.05 mcg/mg in non-pasteurized fertile egg yolk. These results indicate that a fertile egg yolk cannot be pasteurized in order to preserve active follistatin.

Example 4

Effect of Spray/Heat Drying of Fertilized Egg Yolks on Follistatin

Fertile egg yolks contain significant concentrations of follistatin. In an effort to identify whether Spray/Heat Drying denatures or affects this source of naturally occurring follistatin, this study was undertaken.

Fertile chicken eggs yolks were separated with commercial separators then heat/spray dried with a commercial aerosolizer and heat kept under 110° Fahrenheit.

The resulting powder was tested for quantity and quality of active follistatin. Testing utilized purchased follistatin standardized for verification. Confirmations were run by ELISA and quantitations by Liquid Chromatography Tandem Mass Spectrometer with third degree fragmentation (Expertox, Deer Park, Tex.).

Results showed no measurable active or viable follistatin. This compares with previous results follistatin levels of 0.11 to 1.05 mcg/mg in non-spray/heat dried fertile egg yolk. These results indicate that a fertile egg yolk cannot be spray/heat dried in order to preserve active follistatin.

Example 5

Effect of Lyophilization of Fertilized Egg Yolks on Follistatin

Fertile egg yolks contain significant concentrations of follistatin. In an effort to identify whether lyophilization denatures or affects this source of naturally occurring follistatin, this study was undertaken.

Thirty dozen fertile chicken eggs yolks and forty-five dozen unfertilized table eggs were freeze dried in a 18 sq. ft. research dryer for 48 hours at −30° Celsius. The resulting powder was tested for quantity and quality of active follistatin. Testing utilized purchased follistatin standardized for verification. Confirmations were run by ELISA and quantitations by Liquid Chromatography Tandem Mass Spectrometer with third degree fragmentation (Expertox, Deer Park, Tex.).

Results showed good levels of active or viable follistatin, comparable with previous results (follistatin levels of 0.11 to 1.05 mcg/mg in non-lyophilized fertile egg yolk). These results indicate that a fertile egg yolk can be lyophilized in order to preserve active follistatin.

Example 6

Effect of Gamma Irradiation of Fertilized Egg Yolks on Follistatin

Fertile egg yolks contain significant concentrations of follistatin. Egg products are usually pasteurized in order to minimize danger of microbe ingestion. Gamma irradiation is a viable alternative to pasteurization. In an effort to identify whether gamma irradiation denatures or affects this source of naturally occurring follistatin, this study was undertaken.

Fertile chicken eggs were gamma irradiated (FTSI, Mulberry, Fla.) with the most common source of gamma rays for food processing, the radioisotope cobalt 60. The eggs were treated cobalt 60 gamma rays in a facility known as an irradiator. The egg yolks were tested for quantity and quality of active follistatin. Testing utilized purchased follistatin standardized for verification. Confirmations were run by ELISA and quantitations by Liquid Chromatography Tandem Mass Spectrometer with third degree fragmentation (Expertox, Deer Park, Tex.).

Results showed no measurable levels of active or viable follistatin. This compares with previous results follistatin levels of 0.11 to 1.05 mcg/mg in non-irradiated fertile egg yolk. These results indicate that a fertile egg yolk cannot be gamma irradiated in order to preserve active follistatin.

Example 7

Comparison of Whole Fertilized Egg Yolks Versus Whole Fertilized Egg Yolk Blastodisc/Membrane in Content of Active Follistatin Fertile egg yolks contain significant concentrations of follistatin. It is hypothesized that the blastodisc and egg yolk membrane have significantly higher concentrations of follistatin than whole egg yolk. In an effort to compare the follistatin levels of these two egg products, this study was undertaken.

Fertile chicken eggs were cracked and separated by hand. The separated yolk was then divided into two. The egg yolk membrane and blastodiscs were extracted by hand using paper filters. The whole egg yolks and the extraction were tested for quantity and quality of active follistatin. Testing utilized purchased follistatin standardized for verification. Confirmations were run by ELISA and quantitations by Liquid Chromatography Tandem Mass Spectrometer with third degree fragmentation (Expertox, Deer Park, Tex.).

Results showed, nearly a double level of follistatin in the extraction versus the whole fertile egg yolk. The extraction follistatin level was 0.84 mcg/mg compared with the whole yolk follistatin level of 0.36 mcg/mg. These results indicate that extracted blastodiscs and yolk membrane of fertile egg yolk is higher in active follistatin than whole egg yolk.

Example 8

Protein Analysis of Lyophilized Fertilized Egg Yolks

Fertile egg yolk contains significant concentrations of follistatin. In an effort to identify the major proteins and corresponding levels contained in fertile lyophilized egg yolk, this study was undertaken.

Analyses of fertilized lyophilized egg yolk were performed using MALDI-TOF mass spectrometry analysis. There are two major proteins detected by MALDI (35 kDa and 45 kDa) and a minor protein (80 kDa) in most samples. This is consistent with SDS-PAGE analysis of the same samples. No major degradation or aggregation, however there are at least four major proteins detected by this method). Performing in-gel digestion and Mass Spectrometer Peptide Mass Fingerprinting determined that follistatin was one of the proteins identified.

Results showed levels of active or viable follistatin comparable with non-lyophilized levels. These results indicate that a fertile egg yolk can be lyophilized and active follistatin will be preserved along with three other proteins.

Example 9

Effect of Ebeam Irradiation of Fertilized Egg Yolks on Follistatin

Fertile egg yolks contain significant concentrations of follistatin. Egg products are usually pasteurized in order to minimize danger of microbe ingestion. In an effort to identify whether electron beam irradiation denatures or affects this source of naturally occurring follistatin, this study was undertaken.

Six samples of lyophilized fertilized egg yolk were irradiated using dual beam electron irradiation, shooting at separate sample levels of: 0.0 kGy (control), 1.03 kGy, 3.00 kGy, 9.80 kGy, 28.58 kGy, and 51.65 kGy. The samples were irradiated with a 10 MeV Electron Beam Linear Accelerator, Manufactured by Varian Oncology—Papaytron Sled Assembly—Part #100010432 REV. A Varian Inc., 3120 Hansen Way, Palo Alto, Calif. 94304-1030

The linear accelerators used were installed in a cell/system designed by L3 Communications (formerly the Titan Corporation) Pulse Sciences Division, located at 2700 Merced Street, San Leandro, Calif. 94577.

The only visible change to the samples were change in pigmentation of a bright yellow at 1 kGy to a pale/whitish yellow at 51 kGy, with different shades of yellow corresponding to kGy level.

Analyses of the six egg yolk samples were performed using MALDI-TOF mass spectrometry analysis (control and 5 dosages). In summary, the five radiation dosages do not seem to cause any obvious degradation or aggregation of the sample.

There are two major proteins detected by MALDI (35 kDa and 45 kDa) and a minor protein (80 kDa) in most samples. This is consistent with SDS-PAGE analysis of the same samples. No major degradation or aggregation, however there are at least four major proteins detected by this method (see earlier results). Performing in-gel digestion and Mass Spectrometer Peptide Mass Fingerprinting supported the identification of follistatin as one of the proteins in the irradiated samples.

Results showed comparable levels of active or viable follistatin regardless of radiation level. These results indicate that a fertile egg yolk can be irradiated with an electron beam and active follistatin will be preserved.

The examples and embodiments described herein are for illustrative purposes only and various modifications or changes suggested to persons skilled in the art are to be included within the spirit and purview of disclosure and scope of the appended claims. All publications, patents, and patent applications cited herein are hereby incorporated by reference for all purposes.

What is claimed is:

1. A method for increasing muscle mass, comprising administering to a subject in need of increased muscle mass a sports nutrition composition comprising at least 1 ng of follistatin per mg of composition and avian egg yolk membrane, wherein the avian egg yolk membrane is dehydrated and free of viable pathogens, and wherein 1 to 200 grams per dose of the sports nutrition composition is administered.

2. The method of claim 1 wherein the sports nutrition composition further comprises a pharmaceutically acceptable ingredient.

* * * * *